United States Patent [19]

Martell

[11] 4,373,535
[45] Feb. 15, 1983

[54] VENTING, SELF-STOPPING, ASPIRATING SYRINGE

[76] Inventor: Michael D. Martell, 5297 Sandoval Ave., Riverside, Calif. 92509

[21] Appl. No.: 293,662

[22] Filed: Aug. 17, 1981

[51] Int. Cl.³ .............................................. A61B 5/00
[52] U.S. Cl. .................................................. 128/765
[58] Field of Search .............. 128/763, 764, 765, 766, 128/767, 218 R, 218 P, 218 PA, 218 NV, 215; 422/101

[56] References Cited

U.S. PATENT DOCUMENTS 4,327,745 5/1982 Ford, Jr. ............................ 128/765

Primary Examiner—John D. Yasko
Attorney, Agent, or Firm—Gausewitz, Carr, Rothenberg & Edwards

[57] ABSTRACT

A syringe comprises a main tubular body, the body being open at one end and receiving a hypodermic needle at the other end, and a plunger, one end of the plunger extending into the body, through the open end thereof, the plunger having a longitudinal passageway therein permitting air flow therethrough. A fluid-tight seal is formed between the outside surface of the plunger and the inside surface of the syringe body. An air permeable filter membrane extends across the first end of the plunger, in the passageway, whereby the body can fill with blood, causing the air in the body to pass through the membrane to the open end of the body. Upon contact with the blood, the membrane swells and seals, automatically stopping the flow of blood. A one way valve extending across the passageway allows the syringe to be used to aspirate in the absence of natural blood pressure.

12 Claims, 5 Drawing Figures

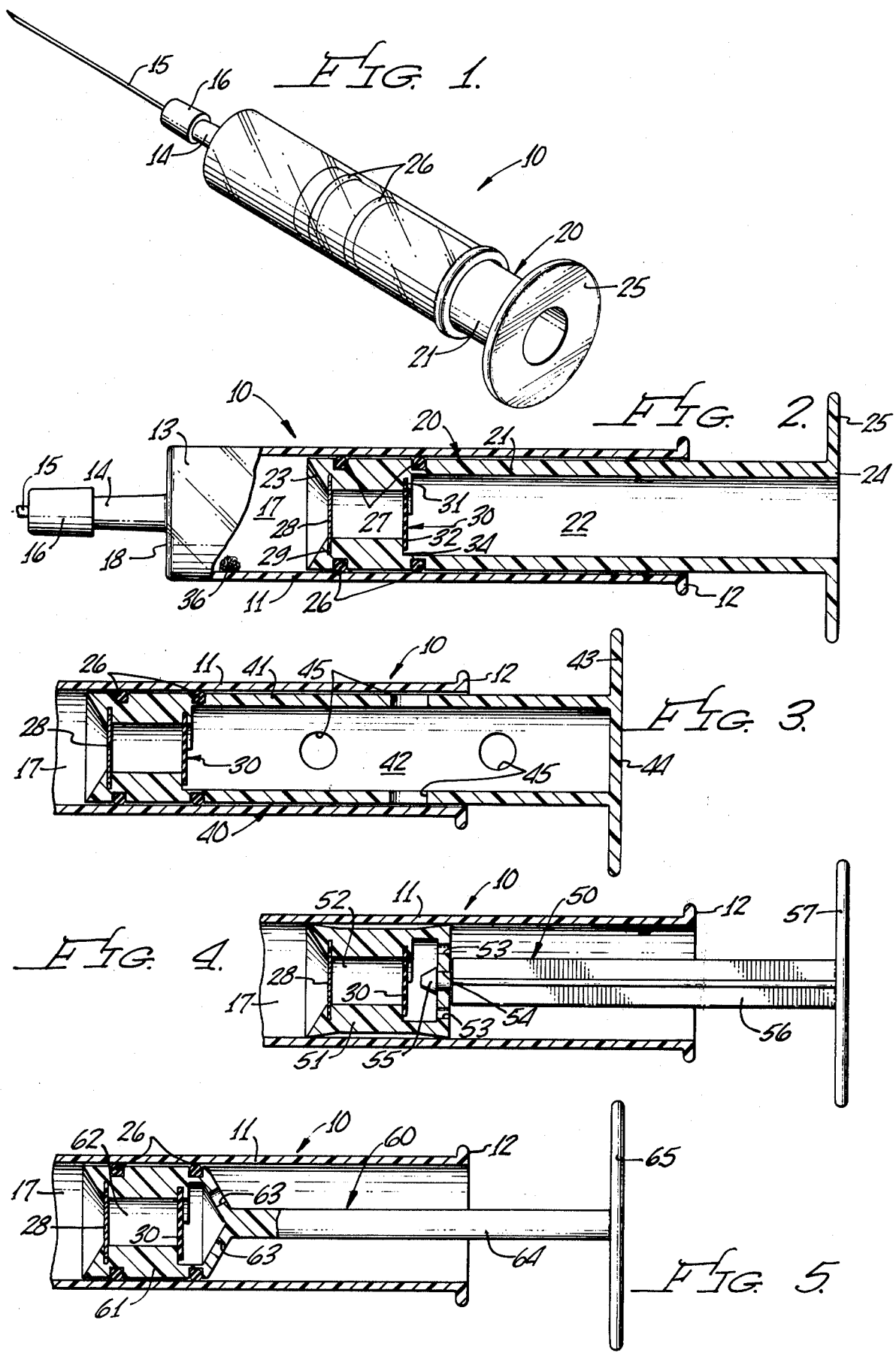

VENTING, SELF-STOPPING, ASPIRATING SYRINGE

BACKGROUND OF THE INVENTION

1. Field of the Invention

The present invention relates to a venting, self-stopping, aspirating syringe and, more particularly, to a syringe which doesn't require a plunger to be pushed back by blood pressure and which does not require a timely withdrawal of the syringe from an artery.

2. Description of the Prior Art

Syringe type devices are typically used for obtaining blood samples to perform a blood gas analysis. Many such blood gas analyses require the drawing of arterial blood which has a sufficient pressure whereby it will, in and of itself, under normal circumstances, fill a syringe without the necessity of aspirating. For this purpose, a conventional syringe type device simply consists of a plunger positioned within a main tubular body. The plunger is fully inserted into the main tubular body and the hypodermic needle punctures the artery. As blood flows into the syringe body, the plunger is pushed back thereby.

There are a variety of problems associated with the use of such a conventional syringe. First of all, the technician must carefully watch the syringe as it is pushed back to note when the required quantity of blood is withdrawn. At the precisely correct time, the syringe is withdrawn from the artery. This requirement for precise timing requires a good deal of skill on the part of the technician.

Furthermore, in obtaining blood samples, it is necessary to use an anti-coagulant to maintain the integrity of the blood sample. Typically, a dilute heparin solution has been placed within the syringe body prior to use, filling the syringe. As the plunger is pushed into the body to expel the liquid heparin, a small quantity, approximately ¼ cc, remains in the syringe, in the area between the end of the plunger and the tip of the hypodermic needle. Therefore, when such a syringe is used to obtain a blood sample to perform a blood gas analysis, the ¼ cc of liquid heparin remains in the syringe. This small amount of heparin represents a contaminant and diluent which interfers with accurate blood gas analysis values and other chemical evaluations.

As a result of the above problems in the use of conventional syringes for obtaining blood samples to perform a blood gas analysis, several syringe devices have been developed to obtain contaminant-free blood samples. An example of such a device is shown in U.S. Pat. No. 4,257,426 to Bailey. In the Bailey patent, a syringe device includes a main tubular body, one end of which slidably receives a combination sealing member and hollow plunger, with the plunger being rotatably connected to the sealing member. The sealing member has several circular lips so that contact sufficient to create a seal exists between the lips on the sealing member and the syringe body. The sealing member has a lateral vent between several of the lips. A flexible thread fixed to the plunger selectively crosses the lips and breaches the seal created by the sealing member to establish communication between the interior of the plunger and the interior of the tubular body via the lateral vent in the sealing member. Removal of the thread allows a seal to be restored so that a gas-free blood sample can be isolated in the hollow tubular body. Crystalline heparin flakes are placed in the body, eliminating the necessity for liquid heparin.

The Bailey syringe has a variety of advantages over a conventional syringe. Initially, through the use of crystalline heparin, the use of liquid heparin can be eliminated, making blood gas analyses more accurate. Secondly, because of the venting action of the plunger, the position of the plunger can be preset so that as the blood rushes into the syringe body, the air crosses the lips, around the flexible thread. As soon as the blood passes the first series of lips, the syringe is removed from the patient and the plunger is rotated, removing the thread from the seal lips, restoring the seal so that the blood sample can be isolated in the hollow tubular body.

While the syringe of the Bailey patent solves some problems associated with conventional syringes, it creates a new set of problems. That is, since the flexible thread extends across the seal lips and breaches the seal created by the sealing member, blood, as well as air, can flow past the sealing member. Accordingly, proper operation of the device still requires removal of the needle at a precise time from the patient. If the syringe is not removed at the precisely correct time, the blood flows past the sealing member and enters the syringe body, on the backside of the sealing member. Then, when the syringe is removed and inverted, this blood escapes.

Furthermore, the use of the syringe of the Bailey patent requires the technician to learn an entirely new procedure, that of rotating the plunger relative to the sealing member to withdraw the thread. In view of the number of technicians which draw blood, this additional training to use the product properly is a significant disadvantage, especially when the operation of the device is not at all apparent from an inspection thereof.

SUMMARY OF THE INVENTION

According to the present invention, there is provided a syringe which solves these problems in a manner unknown heretofor. The present syringe completely prevents the problem of overfilling because it fills on its own and stops automatically when full. The present syringe does not require a technician to watch the plunger carefully as it moves through the syringe body. Rather, the position of the plunger can be preset to obtain a precise quantity of blood. When this quantity of blood has been acquired, the flow of blood stops. Furthermore, this stopping of the blood flow occurs whether or not the syringe is immediately extracted from the patient so that the timing problems of all prior art syringes is completely eliminated. Still further, the present syringe does not require any additional step, such as the rotation of one member relative to another, as in the syringe of the Bailey patent. Once the flow of blood stops, the blood is automatically sealed within the hollow tubular body.

The present syringe also permits the use of dry-flake heparin so that the problems associated with liquid heparin are also eliminated. Finally, the present syringe can be used in an aspirating mode in those situations where individuals have insufficient blood pressure to fill the body of the syringe.

Briefly, the present syringe comprises a main tubular body being open at one end thereof and being adapted to receive a hypodermic needle at the other end thereof; a plunger, one end of the plunger being extendable into the body, through the open end thereof, the plunger having a longitudinal passageway therein permitting air flow therethrough; means forming a fluid-tight seal between the outside surface of the plunger and the inside surface of the body; an air permeable filter membrane extending across the first end of the plunger, in the passageway; and a valve extending across the passageway, between the membrane and the open end of the body, the valve permitting passage of air through the passageway in one direction only, from the first end of the plunger to the open end of the body.

OBJECTS, FEATURES AND ADVANTAGES

It is therefore an object of the present invention to solve the problems encountered heretofor in providing a syringe device for taking blood samples. It is a feature of the present invention to solve these problems by providing a syringe device including a plunger having a passageway therein and an air permeable filter membrane and a one way valve extending across the passageway. An advantage to be derived is a syringe in which dry flake heparin can be used. A further advantage is a free venting syringe. A still further advantage is a syringe in which blood flow stops automatically. Another advantage is a syringe which does not permit blood leakage. Still another advantage is a syringe in which no additional steps are needed to prepare the syringe for aspiration. Another advantage is a syringe which requires no additional training for the use thereof. An additional advantage is a syringe which can be used both for obtaining arterial blood and in an aspirating mode.

Still other objects, features, and attendant advantages of the present invention will become apparent to those skilled in the art from a reading of the following detailed description of the preferred embodiments constructed in accordance therewith, taken in conjunction with the accompanying drawings wherein like numerals designate like or corresponding parts in the several figures and wherein:

BRIEF DESCRIPTION OF THE DRAWINGS

FIG. 1 is a perspective view of a first embodiment of syringe constructed in accordance with the teachings of the present invention;

FIG. 2 is a longitudinal sectional view of the syringe of FIG. 1; and

FIGS. 3, 4 and 5 are longitudinal sectional views of alternate embodiments of plungers for use in the syringe of FIG. 1.

DESCRIPTION OF THE PREFERRED EMBODIMENTS

Referring now to the drawings and, more particularly, to FIGS. 1 and 2 thereof, a preferred form of syringe, generally designated 10, includes a transparent or translucent main tubular body 11 of circular transverse section having an open end 12 and a closed end 13 having a neck 14 which protrudes axially from end 13. A hypodermic needle 15 is frictionally connected to or screwed onto neck 14 by a needle hub 16. Neck 14 is hollow and communicates with an interior chamber 17 generally defined by the space in tubular body 11, the end wall 18 of body 11 and a hollow plunger, generally designated 20, which is received in tubular body 11, through open end 12 thereof.

According to the embodiment of the present invention shown in FIGS. 1 and 2 thereof, plunger 20 includes a transparent or translucent, hollow, cylindrical body 21 having a longitudinal passageway 22 therein permitting air flow therethrough from a first end 23 thereof, which extends into body 11, to the other end 24 thereof, which includes a transverse disc heading 25. At least one, but preferably two, O-rings 26 are positioned in grooves 27 surrounding plunger body 21, adjacent end 23 thereof. O-rings 26 are adapted to slide along the interior surface of main tubular body 11 in a sealed relationship therewith.

An air permeable filter membrane 28 extends across end 23 of plunger 20, across passageway 22. Membrane 28 may be formed from any one of a large number of different materials, such as a fibrous paper material, and has a generally disc-shape thereby to extend into and be sealed in a groove 29 in end 23 of plunger 21. Also, positioned across passageway 22, between membrane 28 and end 24 of plunger 20, is a valve 30 which permits passage of air through passageway 22 in only one direction, from membrane 28 to open end 24 of plunger 20. Valve 30 may simply be a thin, disc-shaped piece of silicon, a portion of the circumference thereof being secured within a groove 31 in plunger body 21 and at least a portion 32 of the circumference thereof being unconnected so as to form a flap, the entire disc 30 resting against a shoulder 34 in plunger body 21. It is obvious that any attempt for air to pass through passageway 22 from open end 24 of plunger body 21 towards membrane 28 will simply compress valve 30 against shoulder 34, preventing such passage. On the other hand, air is free to pass in the opposite direction because of the action of the air lifting valve 30 off of shoulder 34.

A pre-prepared dry flake of heparin 36, prepared in any known manner, can be placed in a dried state in the interior of chamber 17 so that any blood received is immediately exposed to the heparin. The heparin flakes 36 can be stored along with syringe 10 for immediate use thereof.

In operation, the only step that is necessary to prepare syringe 10 for use is the positioning of plunger body 21 so that end 23 is located at a point along tubular body 11 corresponding to the volume of blood sample desired. Typically, syringe bodies are calibrated in volumetric units in order to facilitate this purpose. Hypodermic needle 15 is connected to neck 14 and is inserted into the artery of the donor patient where the blood pressure will normally force the blood through needle 15 into interior chamber 17 of syringe body 11. The technician taking the sample should orient syringe 10 so that membrane 28 is at the furthest distance possible from the rising level of the blood as it enters chamber 17.

As pressure builds up in chamber 17, air is pushed up chamber 17, through permeable membrane 28 and past valve 30, through passageway 22, where it freely exits out of the open top of plunger body 21. Accordingly, passageway 22, membrane 28 and valve 30 serve as a vent for air which was preexistent in chamber 17. It will therefore be appreciated that as the blood fills chamber 17, chamber 17 is continuously purged of all gaseous materials that might contaminate the blood sample.

As the blood pushes all of the air out of chamber 17, it eventually comes into contact with membrane 28. A material is selected for membrane 28 so that upon contact of the blood with membrane 28, the fibers of the membrane swell, arresting the flow of blood. Numerous materials are available which permit air passage therethrough, but will prevent the flow of blood therethrough.

At this point, the flow of blood automatically stops. It is not necessary to immediately withdraw needle 15 from the donor patient so that timing is not critical. It is further not necessary to rotate any portion of or in any other way manipulate any portion of syringe 10. Syringe 10 can be removed and needle 15 inserted into a cork or other sealing member and the blood is fully trapped within chamber 17.

The inclusion of one way valve 30 provides an additional feature for syringe 10. That is, there are circumstances when the donor patient does not have a blood pressure which is high enough to fill chamber 17 without creating a vacuum to draw the blood. This occurs with critically ill patients whose blood pressure is so low that it is difficult to get any flow whatsoever into a conventional syringe device. In any event, it should be apparent that syringe 10 can be used as a conventional syringe without any special preparation. That is, end 23 of plunger barrel 21 can be brought into contact with end wall 18 of plunger body 11 and, after needle 15 is inserted into the donor patient, plunger body 21 can be withdrawn, as in a conventional syringe. Since valve 30 will not permit passage of air through passageway 22 into chamber 17, a vacuum will be created within chamber 17 to permit withdrawal of blood from the donor patient.

It will be apparent that main tubular body 11 has essentially the same configuration as in a conventional syringe, the distinguishing characteristics of syringe 10 being in plunger 20. While plunger 20 shown in FIGS. 1 and 2 incorporates the teachings of the present invention, other configurations of plungers are possible.

Referring now to FIG. 3, there is shown a plunger, generally designated 40, for use in the present invention. Plunger 40 is similar to plunger 20 in that it includes an elongate, hollow body 41 forming a chamber or passageway 42 having a heading 43 at one end thereof and a gas permeable membrane 28 and a one way valve 30 at the other end thereof. O-rings 26 form a seal. Plunger body 41 is not open at end 44 thereof, but rather, a plurality of vent holes 45 are formed in body 41 to permit escape of air.

Referring now to FIG. 4, there is shown a plunger 50 which is made in two separate pieces. One piece consists of a soft rubbery plastic sealing member 51 which would be freely slidable within body 11, eliminating the necessity for O-rings. Sealing member 51 would have a passageway 52 extending therethrough which would be blocked by membrane 28 and valve 30. Sealing member 51 would have a series of vent holes 53 surrounding a central hole 54 which would receive a nipple 55 connected to one end of a hard plastic rod 56 which forms the main portion of the plunger body. The other end of rod 56 would terminate in a heading 57.

Referring now to FIG. 5, there is shown a plunger, generally designated 60, which again would be constructed of a single piece of hard plastic. Plunger 60 has an enlarged portion 61 at one end thereof which is basically similar in construction to sealing member 51, including a passageway 62, a membrane 28, and a one way valve 30. In this case, O-rings 26 again provide the seal with the interior surface of syringe body 11. A series of vent holes 63 permit passage of air from chamber 62 into the interior of body 11. A hard plastic rod 64 has one end thereof made integral with portion 61 and the other end made integral with a heading 65. It will be apparent that plungers 40–60 operate in the same manner as plunger 20.

It can therefore be seen that according to the present invention, there is provided a syringe 10 which solves the problems encountered heretofor in a unique and unobvious manner. Syringe 10 completely prevents the problem of overfilling because it fills on its own and stops automatically when full. Syringe 10 does not require a technician to carefully watch plunger 20, 40, 50 or 60 as it does not move through main body 11. Rather, the position of the plunger can be preset to obtain a precise quantity of blood. When this quantity of blood has been acquired, the flow of blood stops. Furthermore, this stopping of the blood flow occurs whether or not syringe 10 is immediately extracted from the patient so that the timing problems of all prior art syringes is completely eliminated.

Syringe 10 does not require any additional step, such as the rotation of one member relative to another, as in the syringe of the Bailey patent. Once the flow of blood stops, the blood is automatically sealed within chamber 17 in body 11.

Syringe 10 also permits the use of crystalline heparin so that the problems associated with liquid heparin are also eliminated. Finally, syringe 10 can be used in an aspirating mode in those situations where individuals have insufficient blood pressure to fill the body of syringe 10.

While the invention has been described with respect to the preferred physical embodiments constructed in accordance therewith, it will be apparent to those skilled in the art that various modifications and improvements may be made without departing from the scope and spirit of the invention. Accordingly, it is to be understood that the invention is not to be limited by the specific illustrative embodiments, but only by the scope of the appended claims.

I claim:

1. A syringe assembly comprising:
   a tubular body open at one end and being adapted to receive a hypodermic needle at the other end thereof;
   a plunger, one end of which is adapted for insertion into said tubular body through said open end, said plunger having a longitudinal passageway for air flow therethrough;
   means for forming a fluid-tight seal between the outside surface of said plunger and the inside surface of said tubular body;
   an air permeable filter membrane extending across said passageway adjacent said one end of said plunger; and
   valve means extending across said passageway between said membrane and said open end of said tubular body for selectively permitting the passage of air through said passageway.

2. A syringe assembly as recited in claim 1, wherein said seal forming means is positioned adjacent said one end of said plunger.

3. A syringe assembly as recited in claim 1, wherein said filter membrane is formed from a fibrous paper material.

4. A syringe assembly as recited in claim 1, wherein said valve means permits the passage of air through said passageway in one direction only, from said one end of said plunger to said open end of said tubular body.

5. A syringe assembly as recited in claim 4, wherein said passageway includes a first portion of a first diameter adjacent said one end of said plunger and a second portion of increased diameter between said first portion and the other end of said plunger thereby forming an internal shoulder connecting said first and second portions and wherein said valve means comprises a thin member of resilient material extending across said passageway against said shoulder, a portion of the circumference of said member being secured to said plunger, another portion of the circumference thereof being unconnected, so that said member forms a flap.

6. A plunger for use with a conventional syringe comprising:
an elongated body having a longitudinal passageway therein for permitting air flow therethrough;
an air permeable filter membrane extending across said passageway adjacent one end of said body; and
valve means extending across said passageway between said membrane and the other end of said body for selectively permitting the passage of air through said passageway.

7. A plunger as recited in claim 6, further comprising means for forming a fluid-tight seal between the perimeter of said body and the inside surface of a tubular syringe body.

8. A plunger as recited in claim 7, wherein said seal forming means comprises at least one O-ring positioned around said perimeter.

9. A plunger as recited in claim 7, wherein said one end of said elongated body comprises a resilient material which is adapted to engage the inside surface of said tubular syringe body to provide said seal forming means.

10. A plunger as recited in claim 6, wherein said filter membrane is formed from a fibrous paper material.

11. A plunger as recited in claim 6, wherein said valve means permits passage of air through said passageway in one direction only, from said one end of said elongated body to the other end thereof.

12. A plunger as recited in claim 11, wherein said passageway includes a first portion of a first diameter adjacent said one end of said elongated body and a second portion of increased diameter between said first portion and the other end of said body thereby forming an internal shoulder connecting said first and second portions and wherein said valve means comprises a thin member of resilient material extending across said passageway against said shoulder, a portion of the circumference of said member being secured to said body, another portion of the circumference thereof being unconnected, so that said member forms a flap.

* * * * *